US006946061B2

(12) United States Patent
Aksela et al.

(10) Patent No.: US 6,946,061 B2
(45) **Date of Patent: *Sep. 20, 2005**

(54) REGENERATION OF A WORKING SOLUTION IN A HYDROGEN PEROXIDE PRODUCTION PROCESS

(75) Inventors: Reijo Aksela, Espoo (FI); Juhani Paloniemi, Kiviniemi (FI)

(73) Assignee: Kemira Oyj, Helsinki (FI)

( * ) Notice: Subject to any disclaimer, the term of this patent is extended or adjusted under 35 U.S.C. 154(b) by 245 days.

This patent is subject to a terminal disclaimer.

(21) Appl. No.: 10/220,957

(22) PCT Filed: Mar. 5, 2001

(86) PCT No.: PCT/FI01/00215

§ 371 (c)(1), (2), (4) Date: Jan. 22, 2003

(87) PCT Pub. No.: WO01/66461

PCT Pub. Date: Sep. 13, 2001

(65) Prior Publication Data

US 2003/0181741 A1 Sep. 25, 2003

(30) Foreign Application Priority Data

Mar. 6, 2000 (FI) ............................................ 20000511

(51) Int. Cl.[7] ........................... C07F 11/00; C07C 37/00
(52) U.S. Cl. ................................. 204/157.6; 204/157.9
(58) Field of Search ............................ 204/157.6, 157.9

(56) References Cited

U.S. PATENT DOCUMENTS

| | | | | |
|---|---|---|---|---|
| 2,901,491 A | | 8/1959 | Eller, Jr. et al. | |
| 3,432,267 A | | 3/1969 | Lee et al. | |
| 3,752,885 A | | 8/1973 | Liebert et al. | |
| 3,965,251 A | | 6/1976 | Shin et al. | |
| 4,946,566 A | | 8/1990 | Stevens et al. | |
| 5,374,339 A | * | 12/1994 | Guillet et al. | 204/157.5 |
| 5,624,543 A | | 4/1997 | Guillet et al. | |
| H1787 H | | 2/1999 | Ogasawara et al. | |
| 6,749,727 B2 | * | 6/2004 | Aksela et al. | 204/157.6 |

FOREIGN PATENT DOCUMENTS

| | | |
|---|---|---|
| DE | 1 273 499 | 7/1968 |
| JP | 39-4474 | 4/1939 |
| JP | 9-278419 | 10/1997 |

OTHER PUBLICATIONS

Ullman's Encyclopedia of Industrial Chemistry (no month, 1989), vol. A 13, pp. 447–457.*

D. Michael P. Mingos, "Microwaves in Chemical Syntheses", *Chemistry &Industry*, Aug. 1994, pp. 596–599.

André Loupy et al., "New Solvent–Free Organic Synthesis Using Focused Microwaves", *Synthesis*, Sep. 1998, pp. 1213–1234.

C. Strauss, "Invited Review. A Combinatorial Approach to the Development of Environmentally Benign Organic Chemical Preparation", *Aust. J. Chem.*, 1999, 52, 83–96, no month.

*Ullman's Encyclopedia of Industrial Chemistry*, vol. A 13, pp. 447–457 (VCH, Winheim, 1989), no month.

Microwave–Enhanced Chemistry, Fundamentals, Sample Preparation, and Applications, edited by H. M. Kingston and S. J. Haswell (American Chemical Society 1997), no month.

* cited by examiner

*Primary Examiner*—Edna Wong
(74) *Attorney, Agent, or Firm*—Burns, Doane, Swecker & Mathis, LLP

(57) ABSTRACT

The invention relates to a method of regenerating hydrogenated and/or oxygenated alkyl anthraquinones and/or alkyl anthrahydroquinones to alkyl anthraquinones and/or alkyl anthrahydroquinones, wherein the reaction is carried out in the presence of a catalyst under electromagnetic irradiation. Additionally the invention relates to a method for regenerating a working solution containing hydrogenation and/or oxidation products of alkyl anthraquinones and/or alkyl anthrahydroquinones dissolved in at least one solvent, wherein said working solution contains alkyl anthraquinone and/or alkyl anthrahydroquinone products being formed during the production of hydrogen peroxide by a cyclic process including alternate reduction and oxidation of the working solution, said method comprising contacting the working solution containing hydrogenation and/or oxidation products of alkyl anthraquinones and/or alkyl anthrahydroquinones with a catalyst under electromagnetic irradiation to convert the hydrogeneration and/or oxidation products of alkyl anthraquinones and/or alkyl anthrahydroquinones to productive alkyl anthraquinones and/or alkyl anthrahydroquinones.

12 Claims, No Drawings

REGENERATION OF A WORKING SOLUTION IN A HYDROGEN PEROXIDE PRODUCTION PROCESS

FIELD OF THE INVENTION

The present invention relates to a method of regenerating hydrogenated and/or oxygenated alkyl anthraquinones and/or alkyl anthrahydroquinones in the presence of a catalyst. More specifically, the present invention relates to a regeneration method of a working solution in a hydrogen peroxide production process utilizing an anthraquinone method. In the working solution various by-products which do not participate in the hydrogen peroxide production are formed when the working solution is aged. According to the invention these by-products can efficiently be converted to anthraquinones and/or anthrahydroquinones effective as reaction media for the production of hydrogen peroxide.

BACKGROUND OF THE INVENTION

In the description of the background of the present invention that follows reference is made to certain structures and methods, however, such references should not necessarily be construed as an admission that these structures and methods qualify as prior art under the applicable statutory provisions. Applicants reserve the right to demonstrate that any of the referenced subject matter does not constitute prior art with regard to the present invention.

In industrial scale, hydrogen peroxide is mainly produced by an anthraquinone process. In this method anthraquinones which are dissolved in an appropriate organic solvent, are used as a reaction media. The organic solvent is usually a mixture of several organic solvents. The solution obtained by dissolving the anthraquinones in the organic solvent is called "a working solution".

The anthraquinones (AQ) in the working solution are subjected to reduction with hydrogen (hereinafter referred to as "the hydrogenation") in the presence of a catalyst (reaction 1) to produce corresponding anthrahydroquinones (AHQ).

Reaction 1

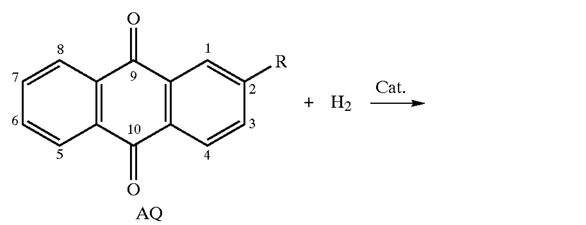

OH

R

OH

AHQ

-continued

R = alkyl

Thereafter the anthrahydroquinones are oxidized with air or with an oxygen containing mixture of gases to convert the anthrahydroquinones into the anthraquinones again (reaction 2). In this oxidation step one mole of hydrogen peroxide is formed per one mole of oxidized anthrahydroquinone.

Reaction 2

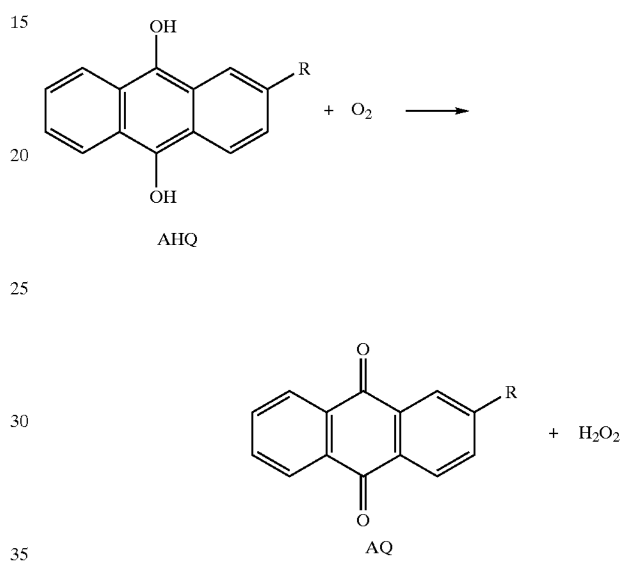

Hydrogen peroxide produced into the working solution after the above mentioned process steps is usually separated from the working, solution by extraction with water.

The working solution from which hydrogen peroxide has been separated is returned to the reduction step again, thereby forming a cyclic process. This process can produce hydrogen peroxide substantially from hydrogen and air, and hence it is an extremely efficient process.

The alkyl anthrahydroquinones (AHQ) and the alkyl anthraquinones (AQ) are subjected to a number of secondary reactions during the cyclic process. Hydrogenation of the aromatic nuclei of AQ yields alkyl tetrahydroanthrahydroquinones (THAHQ) (see reaction 4).

While this hydrogenation and oxidation procedure is repeated, alkyl tetrahydroanthraquinone epoxides (reaction 3a), alkyl hydroxyanthrones (e.g. oxanthrone, reaction 3b) and the like are produced by side reactions. Alkyl tetrahydroanthraquinone epoxides, alkyl hydroxyanthrones and the like compounds cannot produce hydrogen peroxide, even when repeatedly subjected to the reduction and oxidation. The production of these useless compounds is relatively small per occurrence of the reduction and oxidation. However, while the circulation is repeated, the abovementioned compounds are accumulated in the working solution and cause various troubles.

Reaction 3a
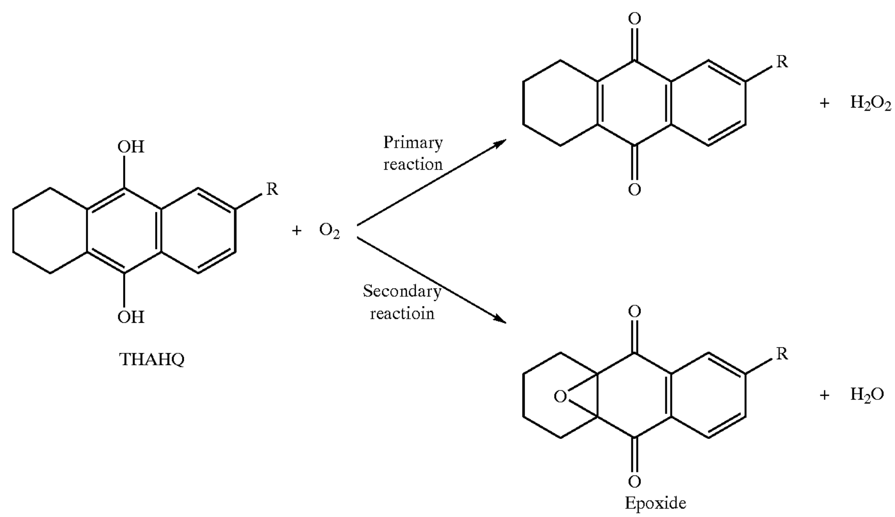
-continued
Reaction 3b
O
R
Cat., $H_2$
O
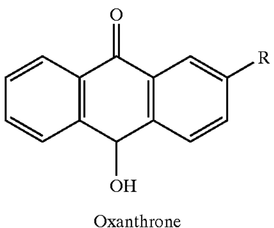
Oxanthrone
Although oxanthrone (see reaction 3b) can be regenerated to active quinone, further hydrogenation leads to anthrone and, subsequently, to dianthrones which cannot be regenerated and thus represent a loss of quinone (reaction 3c).
Reaction 3c
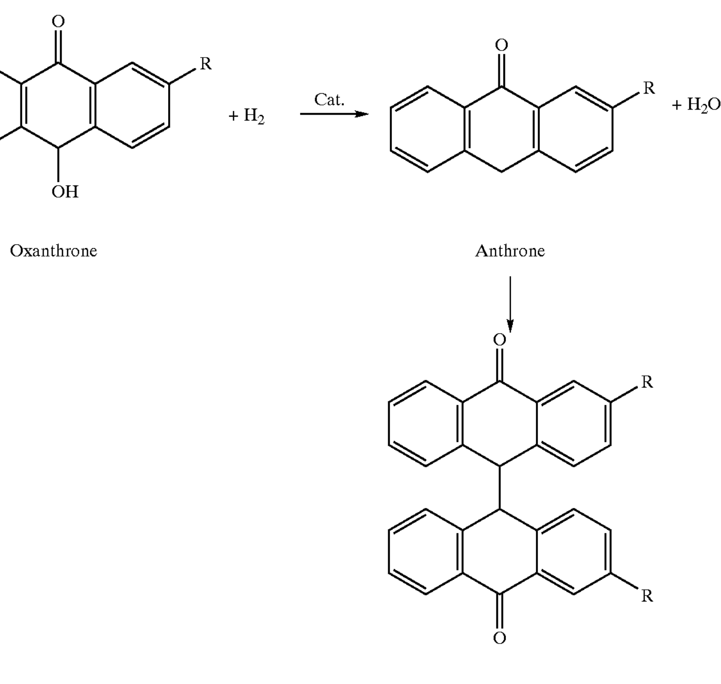

If the nuclei of the alkyl anthraquinones are hydrogenated, the alkyl tetrahydroanthrahydroquinones (THAHQ's or "tetra") are produced (reaction 4). THAHQ's have an ability to produce hydrogen peroxide by the repetition of the reduction and oxidation like the alkyl anthraquinones.

Reaction 4

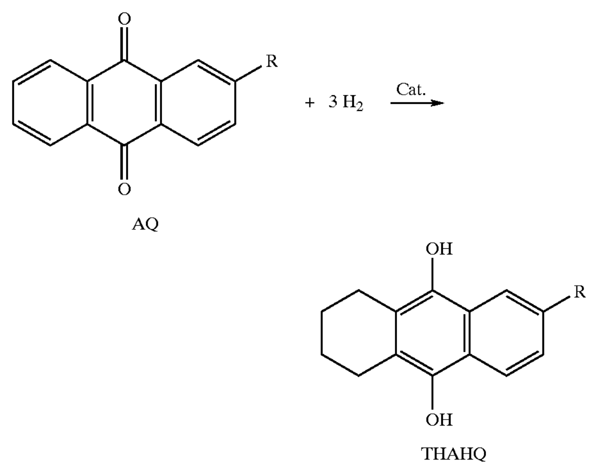

If "tetra" formation is not suppressed during hydrogenation or "tetra" is not hydrogenated, an equilibrium is reached, in which the hydroquinone charged to the oxidizer consists exclusively of 2-alkyl-5,6,7,8-tetrahydroanthrahydroquinone (THAQ). Such a system is called an "all-tetra" system. Even in the all-tetra system it is essential to maintain a certain equilibrium between AQ's and THAQ's in order to avoid the formation of further by-products.

The oxidation rate of the THAHQ's is lower than the oxidation rate of AHQ's. As indicated by U.S. Pat. No. 3,752,885, when the THAQ's are used as the media for the reduction and oxidation, an extremely large energy is required in the oxidation step, and hence half or more of the total energy required in a circulation process is consumed in the oxidation step.

It is known from the recent literature concerning organic synthesis that the reaction times of organic reactions are remarkably reduced when the energy necessary for the occurrence of the reaction is introduced to the system by using electromagnetic irradiation.

For example, the principles of the use of microwave irradiation in chemistry are described in detail for example in the book "Microwave-Enhanced Chemistry, fundamentals, sample preparation and applications" edited by H. M. Kingston and S. J. Haswell (American Chemical Society 1997). The microwave region in the electromagnetic spectra corresponds to the wavelengths 1–100 cm and the frequencies from 30 GHz to 300 MHZ, respectively. According to an international agreement, the frequencies 6.78 MHZ, 13.56 MHZ, 27.12 MHZ, 40.68 MHZ, 915±25 MHZ, 2450±13 MHZ, 5800±75 MHZ and 22125±125 MHZ of the electromagnetic irradiation are committed to industrial and scientific use. The apparatus generating microwave energy is called a magnetron or a klystron. The commonly used magnetrons operate at 2.45 GHz frequency corresponding a wavelength of 12.2 cm, whereas klystrons operate at 915 MHZ frequency corresponding a wavelength of 32.8 cm.

There is a wide and continuously increasing literature available in the area of using microwave techniques in organic synthesis. An example of a short summary article of this topic was published by Mingos in 1994 (D. Michael P. Mingos; "Microwaves in chemical synthesis" in *Chemistry and industry* 1. August 1994, pp. 596–599). Loupy et. al. have recently published a review concerning heterogenous catalysis under microwave irradiation (Loupy, A., Petit, A., Hamelin, J., Texier-Boullet, F., Jachault, P., Mathe, D.; "New solvent-free organic synthesis using focused microwave" in Synthesis 1998, pp. 1213–1234). Another representative article of the area is published by Strauss (C. R. Strauss; "A combinatorial approach to the development of Environmentally Benign Organic Chemical Preparations", an invited review in *Aust. J. Chem.* 1999, 52, 8–'1–96).

Further, alkyl tetrahydroanthraquinones (THAQ's) are hydrogenated to alkyl octahydroanthrahydroquinones (OHAHQ's or "octa", reaction 5).

Reaction 5

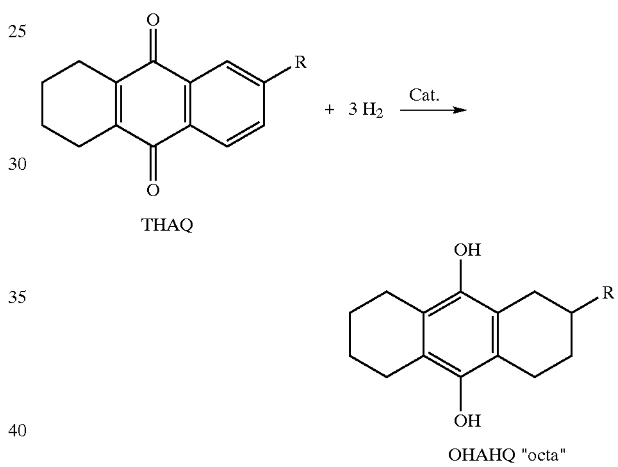

Although these octahydro hydroquinones (OHAHQ) are oxidized by oxygen to the respective octahydro quinones (OHAQ's) with the formation of hydrogen peroxide, the reaction is too slow to be important in the formation of hydrogen peroxide. Therefore, until now, "octa" has been regarded as a decomposition product that cannot be regenerated to useful quinone.

In order to avoid the accumulation of the unwanted anthraquinone products, OHAQ, THAQ epoxides, anthrones and oxanthrones to the working solution, subsequent regeneration steps are necessary. It is a commonly known technique, described for example in *Ullman's Encyclopedia of Industrial Chemistry*, vol. A 13, pp. 447–457 (VCH, Weinheim, 1989) to possess a side-stream of a hydrogenated solution containing THAQ epoxides in contact with basic alpha or gamma aluminum oxide at temperatures 50–140° C. In accordance to this, a German patent DE 1,273,499 (in 1964) describes the conversion of the THAQ epoxide to THAQ via the reduction of one mole of THAQ hydroquinone in the presence of basic alumina catalyst (reaction 6).

Reaction 6

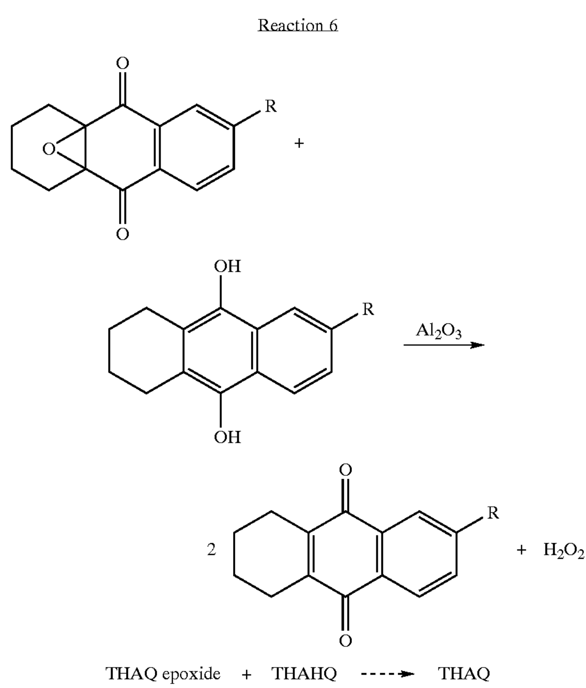

In the optimal working solution, even in the "all-tetra" system, it is essential to have both anthraquinones and tetrahydroanthraquinones present in the working solution. Therefore, another commonly used regeneration step in the hydrogen peroxide process is the regeneration of THAQ's to AQ's (reaction 7). This regeneration step, described for example in US statutory invention registration H 1787 (1999), is commonly performed by possessing an oxidized working, solution container, THAQ's in contact with alumina at temperatures 50–100° C. As the net reaction, three moles of THAQ is converted to one mole of AQ and two moles of THAQ hydroquinone.

Reaction 7

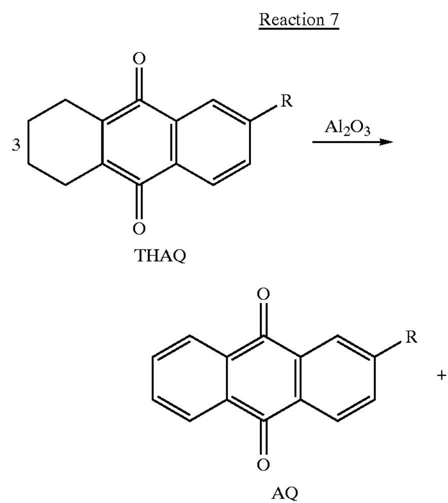

-continued

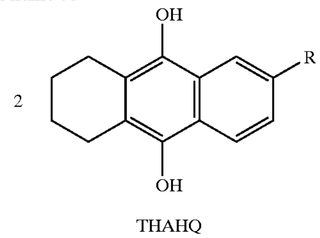

Alternative methods for the regeneration of the working solution used in the production of hydrogen peroxide, appear in the old literature. In U.S. Pat. No. 2,901,491 (1959) is described a method for separation of the active anthrahydroquinones from a hydrogenated old working solution by extraction with a metal hydroxide solution. The anthrahydroquinone salts are further oxidized to anthraquinones and added to the new working, solution as purified compounds.

This method is extremely laborous and expensive. Therefore, it has not been taken into industrial use.

For example, in U.S. Pat. No. 3,432,267 there has been reported that the regeneration of the working solution can be accomplished by treating the working solution with ozone, further treating it with an aqueous caustic soda solution, and then passing it through active alumina at 70 to 75° C. However, this regeneration method comprises 3 steps and it is complicated, and since expensive ozone is used problems regarding economy and an apparatus are present.

In U.S. Pat. No. 3,965,251 there has been suggested a method for regenerating the alkyloxyanthrones by treating the working solution at 130° C. in the presence of a catalyst supporting palladium by the use of an olefin. A large amount of the olefin and the expensive platinum group metal are used in this method. Therefore, this method is also considered to be an economically disadvantageous process.

Furthermore, as a method for converting the alkyl tetrahydro-anthraquinones to the alkyl anthraquinones, Japanese Patent application No. 4474/1964 (JP Kokai 39-4474) has reported that the alkyl tetrahydro-anthraquinones can be converted to the alkyl anthraquinones by bringing alumina, magnesia, a spinel of magnesia-alumina or a metal having a hydrogenation ability such as palladium, platinum or nickel into contact with the working solution and a compound having an unsaturated bond, such as an olefin. Also in this case, however, in order to heighten a reaction rate, a large amount of the olefin is used and the employment of the expensive platinum group metal is required. Hence, the reported method is also considered to be an economically disadvantageous process.

When the regeneration steps are performed by treating the working, solution by aluminum oxide, remarkable amounts of aluminum oxide are needed. Furthermore, the aluminum oxide is deactivated by water formed in the regeneration step. The aluminum oxide is also gradually covered by polymeric aromatic by-products resulted from the polymerization of the aromatic compounds of the aromatic solvent, nowadays most commonly used in the working solution. Therefore, the aluminum oxide used for the regeneration steps must be changed occasionally. The regenerating of the working solution is a costly and sometimes a limiting step of the process. Any improvement in increasing the effectivity of the regeneration steps or the life time of the aluminum oxide will result in substantial savings in the cost of the production of hydrogen peroxide.

Since the used aluminum oxide is contaminated by anthraquinone derivatives and by the phenolic derivatives, the purification of the used aluminum oxide discharged from the hydrogen peroxide process is extensively studied by the applicants. However, the purification of the used aluminum oxide has been found too expensive to carry out. Being a relatively non-toxic material, it is commonly stored to the landfill areas. However, the storage of the used aluminum oxide to the landfill areas possesses an environmental problem at least by occupying a remarkable space in the landfill area. Therefore, also from an environmental point if view, it is extremely desirable to reduce the consumption of aluminum oxide in the production of hydrogen peroxide.

SUMMARY OF THE INVENTION

An objective of the present invention is to obtain a more effective method of regenerating the non-productive anthraquinones and anthraquinone derivatives of the hydrogen peroxide working solution. Since in the optimum composition of the working solution also anthraquinones are present in the working solution, the improvement of the regeneration of THAQ's to AQ's would yield an increase in capacity of the hydrogen peroxide production in cases where the regeneration step is the limiting step of the process.

Furthermore, a goal of the present invention is to develop a method to convert octahydro anthraquinones, oxanthrones or other further reacted by-products of anthraquinones present in the aged working solutions to quinones capable of producing hydrogen peroxide.

In the course of a intensive research work, the inventors have found that the regeneration of the working solution by using alpha or gamma aluminum oxide is remarkably improved when the reaction is performed under electromagnetic irradiation.

According to one aspect, the present invention encompasses a method of regenerating hydrogenated and/or oxygenated alkyl anthraquinones and/or alkyl anthrahydroquinones comprising reacting the alkyl anthraquinones and/or alkyl anthrahydroquinones under electromagnetic irradiation to produce alkyl anthraquinones and/or alkyl anthrahydroquinones.

According to another aspect, the present invention encompasses a method for regenerating a working solution containing hydrogenation and/or oxidation products of alkyl anthraquinones and/or alkyl anthrahydroquinones dissolved in at least one solvent wherein said working solution contains alkyl anthraquinone and/or alkyl anthrahydroquinone products being formed during the production of hydrogen peroxide by a cyclic process including alternate reduction and oxidation of the working solution, the method comprising contacting the working solution containing hydrogenation and/or oxidation products of alkyl anthraquinones and/or alkyl anthrahydroquinones with a catalyst under electromagnetic irradiation to convert the hydrogenation and/or oxidation products of alkyl anthraquinones and/or alkyl anthrahydroquinones to productive alkyl anthraquinones and/or alkyl anthrahydroquinones.

DETAILED DESCRIPTION OF THE INVENTION

In a first aspect of the present invention there is provided a method of regenerating hydrogenated and/or oxygenated alkyl anthraquinones and/or alkyl anthrahydroquinones to alkyl anthraquinones and/or alkyl anthrahydroquinones, wherein the reaction is carried out in the presence of a catalyst under electromagnetic irradiation.

According to one embodiment of this method a tetrahydro alkyl anthraquinone and/or tetrahydro alkyl anthrahydroquinone and/or tetrahydro alkyl anthraquinone epoxide and/or tetrahydro alkyl anthrahydroquinone epoxide is converted to the corresponding alkyl anthraquinone and/or alkyl anthrahydroquinone.

According to another embodiment of this method an octahydro alkyl anthraquinone and/or octahydro alkyl anthrahydroquinone and/or octahydro alkyl anthraquinone epoxide is converted into the form of corresponding tetrahydro alkyl anthraquinone or tetrahydro alkyl anthrahydroquinone or alkyl anthraquinone or alkyl anthrahydroquinone or a mixture thereof.

In a second aspect of the present invention there is provided a method for regenerating a working solution containing other anthracene products accumulated into the working solution during the hydrogenation and oxidation cycle, said method comprising contacting the working solution containing anthracene products with a catalyst under electromagnetic irradiation to convert the anthraquinone and/or anthrahydroquinone side-products to alkyl anthraquinones and/or alkyl anthrahydroquinones capable of producing hydrogen peroxide.

Alternatively, the anthracene products described above could be isolated, dissolved into at least one solvent and contacted with a catalyst under electromagnetic irradiation to convert the anthracene products to alkyl anthraquinones capable of producing hydrogen peroxide.

The frequency of the electromagnetic irradiation can be selected from the frequencies 6.78 MHZ, 13.56 MHZ, 27.12 MHZ, 40.68 MHZ, 915 MHZ and 2450 MHZ.

The electromagnetic energy is preferably introduced at the frequency of about 2450 MHZ or 915 MHZ. The power level can be, for example, from 10 W to 2000 kW.

The electromagnetic irradiation is preferably microwave irradiation.

Conventional catalysts can be used in the methods of the present invention, such as aluminum oxide, including alfa-aluminum oxide and gamma-aluminum oxide. Also other catalysts, such as zeolites, magnesium oxide and silicates, for example, magnesium or zinc, or calcium silicates can be used in the regeneration. The particle size of the catalyst can be from 0.1 mm to 5 mm, preferably from 0.5 mm to 2.4 mm.

Said hydrogenated or oxygenated alkyl anthraquinone product formed in the cyclic anthraquinone process and to be converted to a productive or more productive alkyl anthraquinone can be a hydrogenated alkyl anthraquinone product selected from the group comprising or consisting of tetrahydro alkyl anthraquinones, octahydro alkyl anthraquinones, tetrahydro alkyl anthraquinone epoxides and mixtures thereof.

In addition, the products to be regenerated can be anthracene products such as anthracene, tetrahydro alkyl anthracene or octahydro alkyl anthracene, oxanthrones or anthraquinones containing hydroxyl groups.

The finding that octahydro alkyl anthraquinones were converted to a mixture of tetrahydro alkyl anthraquinones and alkyl anthraquinones by treating the working solution with the catalyst, preferably aluminum oxide, under electromagnetic irradiation was surprising, and constitutes a significant improvement to the existing regeneration techniques. Under the regeneration conditions of the prior art where aluminum oxide is used as a catalyst, it is not possible to convert octahydro alkyl anthraquinones back to alkyl anthraquinones.

The method of the present invention for regenerating anthraquinone and/or anthrahydroquinone by-products under electromagnetic irradiation is applicable to working solutions where 2-amyl anthraquinone (e.g. 2-sec. amyl anthraquinone), 2-methyl anthraquinone, 2-ethyl anthraquinone, 2-isopropyl anthraquinone, 2-butyl anthraquinone (e.g. 2-isobutyl anthraquinone or 2-t-butyl anthraquinone), 1,3-diethyl anthraquinone, 2,3-dimethyl anthraquinone, 1,4-dimethyl anthraquinone, 2,7-dimethyl anthraquinone or combinations of the above mentioned anthraquinones, or the corresponding anthrahydroquinones are used as a reaction media in the preparation of hydrogen peroxide. The most preferred anthraquinones are 2-ethyl, 2-amyl and 2-t-butyl anthraquinones.

The method of the present invention for regenerating anthraquinone by-products under electromagnetic irradiation is applicable to working solutions where aromatic hydrocarbons, organic phosphates, alkylated ureas, organic carboxylic acid esters, alcohols or alkyl carbamates are used as solvents of the anthraquinones or anthrahydroquinones. More preferably, the method is applicable to the regeneration of working solutions where an aromatic crude oil distillate from the boiling point range of from 100° C. to 250° C. is used as the main anthraquinone solvent and a tetra-alkylated urea derivative or a trialkyl phosphate or an alkyl carbamate or a combination thereof is used as the main anthrahydroquinone solvent.

As an example of aromatic solvents can be mentioned commercial crude oil distillates (trade names Shellsol A, Shellsol AB, Shellsol NF, Exxon Solvesso or SureSol). As examples of suitable anthrahydroquinone solvents can be mentioned tetrabutylurea, cyclic urea derivatives, 2-ethythexyl phosphate, tributhyl phosphate and trioctyl phosphate. In addition carboxylic acid esters, for example methyl cyclohexyl acetate, and $C_4$–$C_{12}$ alcohols are suitable anthrahydroquinone solvents. As a suitable aliphatic alcohol, 2-ethylhexanol can be mentioned.

The above mentioned solvents are representative examples of useful solvents in the process. However, the present invention covers the use of microwave techniques in the regeneration of anthraquinone by-products of the working solution of the hydrogen peroxide production also when any other solvents or solvent combinations are used.

The regeneration method of the present invention can be carried out in a slurry reactor, fixed bed reactor, fluidized bed reactor, batch reactor or continuous flow reactor.

The regeneration method of the present invention is preferably carried out at a temperature of from 25° C. to 250° C.

According to the present invention the regeneration can be subjected to a portion of the working solution containing hydrogenation and oxidation products separated from the cyclic process for the production of hydrogen peroxide, as a side-stream, and the upgraded side-stream is then recirculated to the cyclic process. This procedure ensures that the anthraquinone by-products are not accumulated in the cyclic process.

The present invention is based on electromagnetic, preferably microwave, enhanced regeneration of the working solution of a hydrogen peroxide production process. The method of the present invention is superior compared to the existing techniques because octahydro alkyl anthraquinones are regenerated to tetrahydro alkyl anthraquinones and alkyl anthraquinones, and tetrahydro alkyl anthraquinones are regenerated to alkyl anthraquinones in a remarkably shortened reaction time compared to the known regeneration techniques.

Thus, when a typical working solution containing tetrahydro alkyl anthraquinones was regenerated by aluminum oxide under electromagnetic irradiation according to the present invention, the reaction time necessary for the conversion of the tetrahydro alkyl anthraquinones to alkyl anthraquinones was diminished to one third or one half of the reaction time necessary for the same conversion under traditional regeneration treatment. These results were obtained by using a working solution containing only tetrahydro alkyl anthraquinones as quinones and by using an old working solution containing tetrahydro alkyl anthraquinones and alkyl anthraquinones withdrawn from the hydrogen peroxide process of the applicant.

As explained above, the present invention is a significant improvement to the existing techniques, because octahydro alkyl anthraquinones have previously not been found to regenerate to tetrahydro alkyl anthraquinones or alkyl anthraquinones under any conditions, unless they have been isolated from the working solution. In an aged working solution of a hydrogen peroxide process, there is a number of other reduced anthraquinone intermediates than octahydro or tetrahydro anthraquinones. These quinone derivatives are not regarded as useful quinones with respect to produce hydrogen peroxide. Such intermediates are for example hexahydro ethyl anthraquinones. These quinone intermediates can also be converted to useful quinones with respect to produce hydrogen peroxide by using the electromagnetic enhanced regeneration method of the present invention.

The effectiveness of the regeneration process is significantly improved when the electromagnetic, preferably microwave, technique is used in the regeneration of the anthraquinone derivatives of an old working solution. This will accomplish the regeneration of the anthraquinone derivatives by using significantly lower amounts of the catalyst, such as aluminum oxide. Furthermore, it is also obvious that the life time of the aluminum oxide will be longer when the regeneration based on the microwave technique is used. This will remarkably diminish the amount of aluminum oxide needed for the production of hydrogen peroxide. This will result in cost savings in the production of the hydrogen peroxide.

From an environmental point of view the smaller use of aluminum oxide in the production of hydrogen peroxide is certainly an improvement.

The invention is described by the following illustrative examples. However, these examples do not limit the invention.

Example 1

| 27.1 g of a working solution containing: | |
|---|---|
| 2-ethyl anthraquinone (EAQ) | 0.2% w/w |
| tetrahydro 2-ethyl anthraquinone (THEAQ) | 0.6% w/w |
| octahydro-2-ethyl anthraquinone (OHEAQ) | 5.0% w/w |

was dissolved in a mixture of an aromatic hydrocarbon solvent (Shellsol AB 75% v/v) and tetrabutyl urea (25% v/v) and was placed in a round-bottom flask. Dry, powdered aluminum oxide (7.5 g, Martinsverk ANV-802), was added to the reaction mixture under nitrogen.

The resulting reaction mixture was placed in a microwave reactor operating at the frequency of 2.45 GHz (Ethos 1600, Milestone Co.) and the working solution was stirred by a magnetic stirrer under microwave irradiation at a power level of 80 W for 60 min. At this power level the temperature of the reaction mixture was maintained at 80° C. during the reaction.

The concentrations of the anthraquinones were determined by gas-liquid chromatography. The reaction products were identified by a gas chromatograph-mass spectrometer. The concentrations of the quinones during the experiment are presented in table 1.

TABLE 1

| | Reaction time (min) | | | |
|---|---|---|---|---|
| Anthraquinone (% w/w) | 0 | 15 | 30 | 60 |
| EAQ | 0.2 | 0.33 | 0.49 | 0.8 |
| THEAQ | 0.6 | 0.6 | 0.61 | 0.64 |
| OHEAQ | 5.0 | 4.9 | 4.7 | 4.2 |
| total | 5.8 | 5.83 | 5.8 | 5.64 |

It was clearly shown by this example, that octahydro ethyl anthraquinone is converted to ethyl anthraquinone under treatment with aluminum oxide enhanced by microwave irradiation. Calculated from the analyses, a total of 11.7% of the octahydroethyl anthraquinone was converted to ethyl anthraquinone or to tetrahydro ethyl anthraquinone.

Example 2: 27.1 g of a working solution containing 2-ethyl anthraquinone (EAQ) 0.45% w/w and tetrahydro 2-ethyl anthraquinone (THEAQ) 6.0% w/w was dissolved in a mixture of an aromatic hydrocarbon solvent (Shellsol AB, 75% v/v) and tetrabutyl urea (25% v/v), and was placed in a round-bottom flask. Dry, powdered aluminum oxide (7.5 g, Martinsverk AN/V-802), was added to the reaction mixture under nitrogen. The resulting reaction mixture was placed in a microwave reactor (Ethos 1600, Milestone Co.) and the working solution was stirred by a magnetic stirrer under microwave irradiation at a power level of 80 W for 60 min. At this power level the temperature of the reaction mixture was maintained at 80° C. during the reaction. The concentrations of the quinones during the experiment are presented in table 2.

TABLE 2

| | Reaction time (min) | | | |
|---|---|---|---|---|
| Anthraquinone (% w/w) | 0 | 15 | 30 | 60 |
| EAQ | 0.45 | 0.95 | 1.41 | 2.9 |
| THEAQ | 6.0 | 5.51 | 5.0 | 3.6 |
| total | 6.45 | 6.46 | 6.41 | 6.50 |

It was clearly shown in this experiment that tetrahydro ethyl anthraquinone is converted to ethyl anthraquinone under treatment with aluminum oxide enhanced by microwave irradiation. Calculated from the analyses, a total of 37.6% of the tetrahydro ethyl anthraquinone was converted to ethyl anthraquinone during a one hour treatment at 80° C.

Example 3: 100 g of a working solution containing 2-ethyl anthraquinone (EAQ) 3.71% w/w, tetrahydro 2-ethyl anthraquinone (THEAQ) 8.3% w/w, and THEAQ epoxide 0.67% w/w was present in a 75/25/5 mixture of an aromatic hydrocarbon solvent, and tetrabutyl urea/tris-2-ethylhexyl phosphate, which was placed in a microwave reactor (Milestone Ethos MR 30) equipped with a magnetic stirrer and a microwave magnetron. The reaction mixture was irradiated with the microwaves at an appropriate power level in order to keep the inside temperature of the reactor at 80° C., for 6 hours. The concentrations of the quinones during the experiment are presented in table 3.

TABLE 3

| | Reaction time (h) | |
|---|---|---|
| Anthraquinone (% w/w) | 0 | 6 |
| EAQ | 3.71 | 5.08 |
| THEAQ | 8.31 | 6.89 |
| THEAQ epoxide | 0.67 | 0.20 |

During this experiment, the average conversion rate of THEAQ to EAQ was 2.8% per hour. The reaction rate of THEAQ to EAQ at the similar conditions without microwave irradiation was 0.83% per hour (see example 5).

Example 4: 100 g of a working solution containing 2-ethyl anthraquinone (EAQ) 3.71% w/w, tetrahydro 2-ethyl anthraquinone (THEAQ) 8.31% w/w, and THEAQ epoxide 0.67% w/w was present in a 75/25/5 mixture of an aromatic hydrocarbon solvent and tetrabutyl urea and tris-2-ethylhexyl phosphate, which was placed in a microwave reactor (Milestone Ethos MR 30) equipped with a magnetic stirrer and a microwave magnetron. The reaction mixture was radiated with the microwaves at an appropriate power level in order to keep the inside temperature of the reactor at 100° C., for 3 hours. The concentrations of the quinones during the experiment are presented in table 4.

TABLE 4

| Anthraquinone (% w/w) | Reaction time (h) 0 | 3 |
|---|---|---|
| EAQ | 3.71 | 5.83 |
| THEAQ | 8.31 | 6.31 |
| THEAQ epoxide | 0.67 | 0.00 |

During this experiment, the average conversion rate of THEAQ to EAQ was 8% per hour. In the comparative example carried out by using the traditional technique of regeneration (example 6) the average conversion of THEAQ to EAQ was 1–2% per hour during the experiment. The THEAQ epoxide was not found from the working solution after 3 hours treatment. This represents a reaction rate of THEAQ epoxide to THEAQ higher than 33% per hour. In the comparative example carried out by using the traditional technique of regeneration (example 6) a significantly slower decrease in the concentration of THEAQ epoxide to THEAQ (8.0–8.7% per hour) was observed.

Example 5: As a comparative example, 500 g of a working solution containing: 2-ethyl anthraquinone (EAQ) 1.1% w/w, tetrahydro 2-ethyl anthraquinone (THEAQ) 10.3% w/w, THEAQ-epoxide 1.47% w/w, Tot.AQ 12.87% w/w was dissolved in a mixture of an aromatic hydrocarbon solvent 75% v/v and tetrabutyl urea 25% v/v, and was placed in a round-bottom flask. The reactor was heated up to the reaction temperature, 80° C. Dry, powdered aluminum oxide (150 g, Martinsverk AN/V-802), was added to the reaction mixture under nitrogen. The reaction mixture was stirred at 80° C. for six hours. The concentrations of the quinones during the experiment are presented in table 5.

TABLE 5

| Anthraquinone (% w/w) | Reaction time (hours) 0 | 1 h | 2 h | 3 h | 4 h | 5 h | 6 h |
|---|---|---|---|---|---|---|---|
| EAQ | 1.1 | 1.3 | 1.5 | 1.6 | 1.7 | 1.8 | 1.8 |
| THEAQ | 10.3 | 10.6 | 10.4 | 10.3 | 10.2 | 10.2 | 10.1 |
| Epoxide | 1.47 | 1.51 | 1.47 | 1.46 | 1.43 | 1.42 | 1.39 |
| Tot.AQ | 12.87 | 13.41 | 13.37 | 13.36 | 13.33 | 13.42 | 13.29 |

In this experiment, an average conversion rate of THEAQ to EAQ was 0. 83% per hour during the 6 hour experiment at 80° C. This is a typical rate of conversion in the regeneration experiment with basic aluminum oxide. It is also noteworthy that the conversion rate of the THEAQ epoxide to THEAQ or EAQ was 0.16% per hour during this experiment.

Compared to the regeneration results by using the microwave technique at the similar conditions (example 3) the reaction rates are significantly lower.

Example 6: As a comparative example, 500 g of a working solution containing 2-ethyl anthraquinone (EAQ) 1.1% w/w, tetrahydro 2-ethyl anthraquinone (THEAQ) 10.3% w/w, THEAQ-epoxide 1.47% w/w Tot.AQ 12.87% w/w was dissolved in a mixture of an aromatic hydrocarbon solvent 75% v/v and tetrabutyl urea 25% v/v and was placed in a round-bottom flask. The reactor was heated up to the reaction temperature, 100° C. Dry, powdered aluminum oxide (150 g, Martinsverk AN/V-802), was added to the reaction mixture under nitrogen. The reaction mixture was stirred at 100° C. for six hours. The concentrations of the anthraquinones during the experiment are presented in table 6.

TABLE 6

| Anthraquinone (% w/w) | Reaction time (hours) 0 | 1 h | 2 h | 3 h | 4 h | 5 h | 6 h |
|---|---|---|---|---|---|---|---|
| EAQ | 1.1 | 1.5 | 1.8 | 2.0 | 2.3 | 2.4 | 2.6 |
| THEAQ | 10.3 | 10.2 | 9.9 | 9.7 | 9.6 | 9.5 | 9.4 |
| Epoxide | 1.47 | 1.38 | 1.27 | 1.16 | 1.06 | 0.97 | 0.89 |
| Tot.AQ | 12.87 | 13.08 | 12.97 | 12.86 | 12.96 | 12.87 | 12.89 |

Some inaccuracy in the analysis of the starting concentrations (reaction time 0 hours) and in the concentrations of EAQ during the experiment is neglected in this calculation. The average conversion of THEAQ to EAQ, calculated from the analyzed concentrations of THEAQ, was 1–2% per hour during the experiment.

In the experiment, where the microwave technique was used, THEAQ was converted to EAQ at the rate of 8% per hour. Some decrease in the concentration of THEAQ epoxide was observed (8.0–8.7% of the THEAQ epoxide per hour). However, in the similar experiment, where microwave technique was used, the THEAQ epoxide was not found after hours treatment. This represents a reaction rate higher than 33% per hour.

While the present invention has been described by reference to the above-mentioned embodiments, certain modifications and variations will be evident to those of ordinary skill in the art. Therefore, the present invention is to limited only by the scope and spirit of the appended claims.

What is claimed is:

1. A method for regenerating a working solution, the working solution containing alkyl anthraquinone and/or alkyl anthrahydroquinone products being formed during the production of hydrogen peroxide by a cyclic process including alternate reduction and oxidation of the working solution and the working solution further containing hydrogenation and/or oxidation products of alkyl anthraquinones and/or alkyl anthrahydroquinones dissolved in at least one solvent, the method comprising contacting the working solution with a catalyst under microwave irradiation to convert the hydrogenation and/or oxidation products of alkyl anthraquinones and/or alkyl anthrahydroquinones to productive alkyl anthraquinones and/or alkyl anthrahydroquinones.

2. The method of claim 1, wherein the hydrogenated and/or oxygenated products of alkyl anthraquinones and/or alkyl anthrahydroquinones comprise hydrogenated and/or oxygenated alkyl anthraquinone products selected from the group consisting of tetrahydro alkyl anthraquinones and/or tetrahydro alkyl anthrahydroquinones, hexahydro alkyl anthraquinones and/or hexahydro alkyl anthrahydroquinones, octahydro alkyl anthraquinones and/or octahydro alkyl anthrahydroquinones, tetrahydro alkyl anthraquinone epoxides and/or tetrahydro alkyl anthrahydroquinone epoxides, hexahydro alkyl anthraquinone epoxides and/or hexahydro alkyl anthrahydroquinone epoxides, octahydro alkyl anthraquinone epoxides, and/or octahydro alkyl anthrahydroquinone epoxides and mixtures thereof and other anthracene and/or anthraquinone and/or anthrahydroquinone products formed into the working solution.

3. The method of claim 1, wherein the catalyst is of any material capable of absorbing the microwave irradiation.

4. The method of claim 3, wherein the catalyst is selected from the group consisting of aluminum oxides, zeolites, magnesium oxide and silicates.

5. The method of claim 3, wherein the catalyst has a particle size from 0.1 mm to 5 mm.

6. The method of claim 1, wherein the alkyl anthraquinone is selected from the 2-ethyl, 2-amyl and 2-t-butyl anthraquinones and/or mixtures of those anthraquinones, and the alkyl anthrahydroquinone is selected from the 2-ethyl, 2-amyl and 2-t-butyl anthrahydroquinones and/or mixtures of those anthrahydroquinones.

7. The method of claim 1, wherein the solvent is selected from the group consisting of aromatic hydrocarbons, organic phosphates, alkylated ureas, organic carboxylic acid esters, alcohols and alkyl carbamates and mixtures thereof.

8. The method of claim 7, wherein the solvent comprises a mixture of a first solvent comprising an aromatic hydrocarbon, and a second solvent selected from the group consisting of tetra-alkylated urea derivatives, trialkyl phosphates and alkyl carbamates and mixtures thereof.

9. The method of claim 1, wherein conversion is carried out in a slurry reactor, fixed bed reactor, fluidized bed reactor, bath reactor or continuous flow reactor.

10. The method of claim 1, wherein conversion is carried out at a temperature of from 25° C. to 250° C.

11. The method of claim 1, wherein a side-steam working solution containing hydrogenation and/or oxidation products is separated from the working solution, and an upgraded side-stream working solution is recirculated to the working solution.

12. The method of claim 1, wherein the microwave irradiation is performed at a frequency selected from the frequencies of 6.78 MHz, 13.56 MHz, 27.12 MHz, 40.68 MHz, 915 MHz and 2450 MHz.

* * * * *